(12) United States Patent
Bocek et al.

(10) Patent No.: US 7,386,344 B2
(45) Date of Patent: Jun. 10, 2008

(54) PACER WITH COMBINED DEFIBRILLATOR TAILORED FOR BRADYCARDIA PATIENTS

(75) Inventors: Joseph M. Bocek, Seattle, WA (US); Richard Milon Dujmovic, Jr., Coon Rapids, MN (US); Phil Foshee, Woodinville, WA (US); Harley White, Carnation, WA (US); Jaeho Kim, Redmond, WA (US); Anthony Harrington, Woodinville, WA (US); Richard S. Sanders, Stillwater, MN (US); Douglas R. Daum, Oakdale, MN (US); Paul De Coriolis, Bellevue, WA (US); Joseph Smith, North Oaks, MN (US); Richard Fogoros, Pittsburg, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 378 days.

(21) Appl. No.: 10/921,777

(22) Filed: Aug. 18, 2004

(65) Prior Publication Data

US 2006/0036288 A1 Feb. 16, 2006

Related U.S. Application Data

(60) Provisional application No. 60/600,614, filed on Aug. 11, 2004.

(51) Int. Cl.
*A61N 1/39* (2006.01)
(52) U.S. Cl. ............................................ 607/5; 607/4
(58) Field of Classification Search .................... None
See application file for complete search history.

(56) References Cited

U.S. PATENT DOCUMENTS

RE30,372 E    8/1980    Mirowski et al.

(Continued)

FOREIGN PATENT DOCUMENTS

WO    WO-0166180 A2    9/2001

(Continued)

OTHER PUBLICATIONS

"International Search Report and Written Opinion for Application No. PCT/US2005/028592, date mailed Jan. 19, 2006", 18 Pages.

(Continued)

*Primary Examiner*—Carl Layno
(74) *Attorney, Agent, or Firm*—Schwegman, Lundberg & Woessner, P.A.

(57) ABSTRACT

A combination pacer/defibrillator is tailored for bradycardia patients. In one example, its shock-delivery specificity exceeds its sensitivity to shockable ventricular tachyarrhythmias. In another example, its specificity exceeds 95%, or 99%, or even 99.5%. Sensitivity is programmed to a high desired sensitivity value, but only if it can be done without decreasing the specificity below the desired specificity threshold value. This can be conceptualized as "avoiding at all costs" delivering false shocks, even at the expense of failing to deliver a shock to a treatable ventricular tachyarrhythmia. Specificity enhancements include, among other things, inhibiting shock delivery when the patient is breathing or not supine, using multiple channels or a high rate VT/VF detection threshold. The present pacer/defibrillator device could potentially save the lives of bradyarrhythmia patients who are not presently clinically indicated for a defibrillator/pacer, but who have an increased risk of sudden cardiac death due to one or more risk factors.

44 Claims, 9 Drawing Sheets

U.S. PATENT DOCUMENTS

| | | |
|---|---|---|
| RE30,387 E | 8/1980 | Denniston, III et al. |
| 4,375,817 A | 3/1983 | Engle et al. |
| 4,693,253 A | 9/1987 | Adams |
| 4,727,877 A | 3/1988 | Kallok |
| 4,774,950 A | 10/1988 | Cohen |
| 4,799,493 A | 1/1989 | DuFault |
| 4,880,005 A | 11/1989 | Pless et al. |
| 4,960,123 A | 10/1990 | Maker |
| 4,986,270 A | 1/1991 | Cohen |
| 4,989,602 A | 2/1991 | Sholder et al. |
| 5,027,816 A | 7/1991 | Cohen |
| 5,048,521 A | 9/1991 | Pless et al. |
| 5,054,485 A | 10/1991 | Cohen |
| 5,083,563 A | 1/1992 | Collins |
| 5,085,213 A | 2/1992 | Cohen |
| 5,105,810 A | 4/1992 | Collins et al. |
| 5,111,816 A | 5/1992 | Pless et al. |
| 5,119,813 A | 6/1992 | Cohen |
| 5,190,034 A | 3/1993 | Sholder |
| 5,191,884 A | 3/1993 | Gilli et al. |
| 5,251,626 A | 10/1993 | Nickolls et al. |
| 5,257,621 A | 11/1993 | Bardy et al. |
| 5,269,300 A | 12/1993 | Kelly et al. |
| 5,311,874 A | 5/1994 | Baumann et al. |
| 5,312,443 A | 5/1994 | Adams et al. |
| 5,318,591 A | 6/1994 | Causey, III et al. |
| 5,325,856 A | 7/1994 | Nitzsche et al. |
| 5,336,253 A | 8/1994 | Gordon et al. |
| 5,350,401 A | 9/1994 | Levine |
| 5,350,406 A | 9/1994 | Nitzsche et al. |
| 5,354,316 A | 10/1994 | Keimel |
| 5,391,188 A | 2/1995 | Nelson et al. |
| 5,431,682 A | 7/1995 | Hedberg |
| 5,439,482 A | 8/1995 | Adams et al. |
| 5,554,174 A | 9/1996 | Causey, III |
| 5,584,868 A | 12/1996 | Salo et al. |
| 5,607,385 A | 3/1997 | Fransischelli et al. |
| 5,662,687 A | 9/1997 | Hedberg et al. |
| 5,713,924 A | 2/1998 | Min et al. |
| 5,720,294 A | 2/1998 | Skinner |
| 5,722,994 A | 3/1998 | Noren et al. |
| 5,738,105 A | 4/1998 | Kroll |
| 5,749,901 A | 5/1998 | Bush et al. |
| 5,766,225 A | 6/1998 | Kramm |
| 5,782,879 A | 7/1998 | Rosborough et al. |
| 5,792,183 A | 8/1998 | Esler |
| 5,836,971 A | 11/1998 | Starkweather |
| 5,836,976 A | 11/1998 | Min et al. |
| 5,851,220 A | 12/1998 | Murphy |
| 5,857,977 A | 1/1999 | Caswell et al. |
| 5,868,793 A | 2/1999 | Nitzsche et al. |
| 5,873,897 A | 2/1999 | Armstrong et al. |
| 5,876,349 A | 3/1999 | Wang et al. |
| 5,882,352 A | 3/1999 | Duncan et al. |
| 5,885,221 A | 3/1999 | Hsu et al. |
| 5,891,170 A | 4/1999 | Nitzsche et al. |
| 5,916,238 A | 6/1999 | Hauser et al. |
| 5,931,857 A | 8/1999 | Prieve et al. |
| 5,951,592 A | 9/1999 | Murphy |
| 5,954,752 A | 9/1999 | Mongeon et al. |
| 5,978,700 A | 11/1999 | Nigam |
| 6,076,014 A | 6/2000 | Alt |
| 6,115,627 A | 9/2000 | Street |
| 6,128,529 A | 10/2000 | Elser |
| 6,151,524 A | 11/2000 | Krig et al. |
| 6,169,923 B1 | 1/2001 | Kroll |
| 6,212,428 B1 | 4/2001 | Hsu et al. |
| 6,223,078 B1 | 4/2001 | Marcovecchio |
| 6,230,055 B1 | 5/2001 | Sun et al. |
| 6,259,947 B1 | 7/2001 | Olson et al. |
| 6,269,267 B1 * | 7/2001 | Bardy et al. .................. 607/5 |
| 6,275,732 B1 | 8/2001 | Hsu et al. |
| 6,317,632 B1 | 11/2001 | Krig et al. |
| 6,324,422 B1 | 11/2001 | Williams et al. |
| 6,327,499 B1 | 12/2001 | Alt |
| 6,370,427 B1 | 4/2002 | Alt et al. |
| 6,393,316 B1 | 5/2002 | Gillberg et al. |
| 6,415,179 B1 | 7/2002 | Pendekanti et al. |
| 6,430,435 B1 | 8/2002 | Hsu et al. |
| 6,442,425 B1 | 8/2002 | Alt |
| 6,445,949 B1 | 9/2002 | Kroll |
| 6,449,503 B1 | 9/2002 | Hsu |
| 6,477,406 B1 | 11/2002 | Turcott |
| 6,484,055 B1 | 11/2002 | Marcovecchio |
| 6,487,443 B2 | 11/2002 | Olson et al. |
| 6,490,478 B1 | 12/2002 | Zhang et al. |
| 6,493,584 B1 | 12/2002 | Lu |
| 6,564,097 B1 | 5/2003 | Williams et al. |
| 6,567,691 B1 | 5/2003 | Stadler |
| 6,611,713 B2 | 8/2003 | Schauerte |
| 6,628,986 B1 | 9/2003 | Mouchawar et al. |
| 6,687,540 B2 | 2/2004 | Marcovecchio |
| 6,748,269 B2 | 6/2004 | Thompson et al. |
| 6,754,527 B2 | 6/2004 | Stroebel et al. |
| 6,754,528 B2 | 6/2004 | Bardy et al. |
| 6,801,806 B2 | 10/2004 | Sun et al. |
| 7,206,633 B2 * | 4/2007 | Saba ........................... 607/14 |
| 2001/0034539 A1 | 10/2001 | Stadler et al. |
| 2002/0002389 A1 | 1/2002 | Bradley et al. |
| 2002/0032469 A1 | 3/2002 | Marcovecchio |
| 2002/0035335 A1 | 3/2002 | Schauerte |
| 2002/0058968 A1 | 5/2002 | Sun et al. |
| 2002/0091333 A1 | 7/2002 | Hsu et al. |
| 2002/0107544 A1 | 8/2002 | Ostroff et al. |
| 2002/0123768 A1 | 9/2002 | Gilkerson |
| 2002/0169483 A1 | 11/2002 | Henry et al. |
| 2002/0188215 A1 | 12/2002 | Ferek-Petric |
| 2003/0032989 A1 | 2/2003 | Herleikson |
| 2003/0045906 A1 | 3/2003 | Stroebel et al. |
| 2003/0060849 A1 | 3/2003 | Hsu |
| 2003/0074026 A1 | 4/2003 | Thompson et al. |
| 2003/0088282 A1 | 5/2003 | Ostroff |
| 2003/0097153 A1 | 5/2003 | Bardy et al. |
| 2003/0105491 A1 | 6/2003 | Gilkerson et al. |
| 2003/0120316 A1 | 6/2003 | Spinelli et al. |
| 2003/0144700 A1 | 7/2003 | Brown et al. |
| 2003/0204209 A1 | 10/2003 | Burnes et al. |
| 2003/0204210 A1 | 10/2003 | Ousdigian et al. |
| 2003/0216654 A1 * | 11/2003 | Xu et al. .................... 600/509 |
| 2004/0111121 A1 | 6/2004 | Brown et al. |
| 2005/0251215 A1 | 11/2005 | Dujmovic, Jr. et al. |

FOREIGN PATENT DOCUMENTS

WO   WO-2006020791 A1   2/2006

OTHER PUBLICATIONS

"3 Abstracts from the Tenth Annual Scientific Congress of the Hong Kong College of Cardiology", *Medical Section*, 7(8), Jun. 21-23, 2002, 11-13.

Albert, C. M., et al., "Prospective Study of Sudden Cardiac Death Among Women in the United States", *Circulation*, 107, (2003),2096-2101.

Boecker, D, et al., "Benefit of an Enhanced Detection Algorithm in Optimizing Treatment of Slow Ventricular Tachycardia", *PACE*, 23 (*Part II*), (Apr. 2000), Abstract 95.

Buxton, A. E., et al., "Relation of Ejection Fraction and Inducible Ventricular Tachycardia to Mode of Death in Patients With Coronary Artery Disease—An Analysis of Patients Enrolled in the Multicenter Unsustained Tachycardia Trial", *Circulation*, 106, (2002),2466-2472.

Chung-Seung, C., "Medical Session—Management of Congestive Heart Failure", *Medical Section*, 7(8), (2002),4-9.

Copie, X., et al., "Predictive Power of Increased Heart Rate Versus Depressed Left Ventricular Ejection Fraction and Heart Rate Variability for Risk Stratification After Myocardial Infarction", *Journal of the American College of Cardiology*, 27(2), (1996),270-276.

Darpö, B., et al., "Incidence of Sudden Death After Radiofrequency Ablation of the Atrioventricular Junction for Atrial Fibrillation", *The American Journal of Cardiology*, 80, (1997),1174-1177.

Dodinot, B., et al., "La Mort Subite Chez le Porteur de Stimulateur Cardiaque", *Annales de Cardiologie et D'Angeiologie*, (1985),161-166.

Engdahl, J., et al., "The Epidemiology of Out-of-Hospital 'Sudden' Cardiac Arrest", *Resuscitation*, 52, (2002),235-245.

Ezekowitz, J. A., et al., "Implantable Cardioverter Defibrillators in Primary and Secondary Prevention: A Systematic Review of Randomized, Controlled Trials", *Annals of Internal Medicine*, 138, (2003),445-452.

Fromer, M., et al., "Experience with a New Implantable Pacer-, Cardioverter-Defibrillator for the Therapy of Recurrent Sustained Ventricular Tachyarrhythmias: A Step Toward a Universal Ventricular Tachyarrhythmia Control Device", *Pace*, 14, (1991),1288-1297.

Furman, S., "The Future of the Pacemaker", Pace, 25(1), (2002),1-2.

Gasparini, M., et al., "Long-Term Follow-Up After Atrioventricular Nodal Ablation and Pacing: Low Incidence of Sudden Cardiac Death", *Pace*, 23(11)(*Part II*), (2000),1925-1929.

Geelen, P., et al., "The Value of DDD Pacing in Patients with an Implantable Carioverter Defibrillator", *Pace*, 20 (*Part II*), (1997),177-181.

Golino, A., et al., "Clinical Experience with the Transvenous Medtronic Pacer Cardioverter Defibrillator (PCD(r)) System", *Texas Heart Institute Journal*, 20(4), (1993),264-270.

Gregoratos, G., et al., "ACC/AHA/NASPE 2002 Guideline Update for Implantation of Cardiac Pacemakers and Antiarrhythmia Devices: Summary Article—A Report of the American College of Cardiology/American Heart Association Task Force on Practice Guidelines", *Journal of Cardiovascular Electrophysiology*, 13(11), (ACC/AHA/NASPE Committee to Update the 1988 Pacemaker Guidelines),(2002),1183-1199.

Grimm, W., et al., "Electrocardiographically Documented Unnecessary, Spontaneous Shocks in 241 Patients With Implantable Cardioverter Defibrillators", *Pace*, 15(11)(*Part 1*), (1992),1667-1673.

Higgins, S. L. et al., "Indications for Implantation of a Dual-Chamber Pacemaker Combined With an Implantable Cardioverter-Defibrillator", *American Journal of Cardiology*, 81(11), (1998),1360-1362.

Hohnloser, S. H., et al., "Changing Late Prognosis of Acute Myocardial Infarction—Impact on Management of Ventricular Arrhythmias in the Era of Reperfusion and the Implantable Cardioverter-Defibrillator", *Circulation*, 107, (2003),941-946.

Iskos, D., et al., "Physiological Cardiac Pacing in Patients With Contemporary Implantable Cardioverter-Defibrillators", *American Journal of Cardiology*, 82(1), (1998),66-71.

Jouven, X., et al., "Predicting Sudden Death in the Population—The Paris Prospective Study I", *Circulation*, 99, (1999),1978-1983.

Kanagaratnam, L., et al., "Matching Approved "Nondedicated" Hardware to Obtain Biventricular Pacing and Defibrillation: Feasibility and Troubleshooting", *Pace*, 25(7), (2002),1066-1071.

Kay, G. N., et al., "The Abate and Pace Trial: A Prospective Study of Catheter Ablation of the AV Conduction System and Permanent Pacemaker Implantation for Treatment of Atrial Fibrillation", *Journal of Interventional Cardiac Electrophysiology*, 2(2), (1998),121-135.

Lamas, G. A., et al., "The Mode Selection Trial (Most) in Sinus Node Dysfunction: Design, Rationale, and Baseline Characteristics of the First 1000 Patients", *American Heart Journal*, 140, (2000),541-551.

Lavergne, T., et al., "Preliminary Clinical Experience with the First Dual Chamber Pacemaker Defibrillator", *Pace*, 20(1) (*Part II*), (1997),182-188.

Liu, B. C., et al., "Inappropriate Shock Delivery and Biventricular Pacing Cardiac Defibrillators", *Texas Heart Journal*, 30(1), (2003),45-49.

Mattioli, A. V., et al., "Causes of Death in Patients with Unipolar Single Chamber Ventricular Pacing: Prevalence and Circumstances in Dependence on Arrhythmias Leading to Pacemaker Implantation", *Pace*, 18(1)(*Part 1*), (1995),11-17.

Morris, M. M., et al., "A Preview of Implantable Cardioverter Defibrillator Systems in the Next Millennium: An Integrative Cardiac Rhythm Management Approach", *American Journal of Cardiology*, 83(5B), (1999),48D-54D.

Myerburg, R. J., et al., "Opportunities for Sudden Death Prevention: Directions for New Clinical and Basic Research", *Cardiovascular Research*, 50, (2001),177-185.

Pinski, S. L., et al., "Permanent Pacing via Implantable Defibrillators", *Pace*, 23(*11 Part 1*), (2000),1667-1682.

Saksena, S., et al., "Long-Term Multicenter Experience With a Second-Generation Implantable Pacemaker-Defibrillator in Patients With Malignant Ventricular Tachyarrhythmias", *Journal of American College of Cardiology*, 19(3), (1992),490-499.

Santini, M., et al., "Indications for Dual-Chamber (DDD) Pacing in Implantable Cardioverter-Defibrillator Patients", *American Journal of Cardiology*, 78(*Supp. 5A*), (1996),116-118.

Singer, I., et al., "The Initial Clinical Experience with an Implantable Cardioverter Defibrillator/Antitachycardia Pacemaker", *Pace*, 14, (1991),1119-1128.

Sweeney, M. O., et al., "Adverse Effect of Ventricular Pacing on Heart Failure and Atrial Fibrillation Among Patients With Normal Baseline QRS Duration in a Clinical Trial of Pacemaker Therapy for Sinus Node Dysfunction", *Circulation*, 107, (2003),2932-2937.

Thackray, S. D., et al., "The Prevalence of Heart Failure and Asymptomatic Left Ventricular Systolic Dysfunction in a Typical Regional Pacemaker Population", *European Heart Journal*, 24, (2003),1143-1152.

Twidale, N., et al., "Predictors of Outcome After Radiofrequency Catheter Ablation of the Atrioventricular Node for Atrial Fibrillation and Congestive Heart Failure", *American Heart Journal*, 136(4)(*Part 1*), (1998),647-657.

Zehender, M., et al., "Prevalence, Circumstances, Mechanisms, and Risk Stratification of Sudden Cardiac Death in Unipolar Single-Chamber Ventricular Pacing", *Circulation*, 85, (1992),596-605.

\* cited by examiner

PACER WITH COMBINED DEFIBRILLATOR TAILORED FOR BRADYCARDIA PATIENTS

CROSS REFERENCE TO RELATED APPLICATION

This patent application claims the benefit of priority, under 35 U.S.C. Section 119(e), to Bocek et al. U.S. Provisional Patent Application Ser. No. 60/600,614, filed Aug. 11, 2004, entitled PACEMAKER WITH COMBINED DEFIBRILLATOR TAILORED FOR BRADYCARDIA PATIENTS.

TECHNICAL FIELD

This patent application pertains generally to implantable cardiac rhythm management devices and more particularly, but not by way of limitation, to a pacer with a combined defibrillator that is tailored for bradyarrhythmia patients.

BACKGROUND

Implantable medical devices include, among other things, cardiac rhythm management (CRM) devices such as pacers, cardioverters, defibrillators, cardiac resynchronization therapy (CRT) devices, as well as combination devices that provide more than one of these therapy modalities to a subject. For example, an implantable defibrillator/pacer is typically configured as an implantable defibrillator with backup pacing capability. Such devices are intended to serve patients having a history of previous ventricular or atrial tachyarrhythmia episodes. Ventricular arrhythmias include ventricular tachyarrhythmia (VT) and dangerous and life-threatening ventricular fibrillation (VF), referred to collectively herein as VT/VF. VT/VF is typically treated with antitachyarrhythmia pacing (ATP) therapy or a defibrillation countershock.

A cardiac rhythm management device's detection scheme for a particular cardiac arrhythmias is typically characterized by its "sensitivity" and "specificity." Sensitivity generally refers to the ability of the detection scheme to effectively detect an abnormal heart rhythm (e.g., VT/VF) that the physician desires the cardiac rhythm management device to treat. The sensitivity can be expressed as follows:

Sensitivity=True Positives/(True Positives+False Negatives)  (Eq. 1)

Specificity generally refers to the ability of the detection scheme to avoid improperly treating rhythms (e.g., sinus tachycardia) that the physician determines that the device should not treat. The specificity can be expressed as follows:

Specificity=True Negatives/(True Negatives+False Positives)  (Eq. 2)

For example, if the rhythm to be detected is VT/VF, then a true positive would occur when a particular rhythm is VT/VF and the detection algorithm correctly declares it as VT/VF. A false negative would occur when the rhythm is VT/VF and the detection algorithm erroneously declares it as not VT/VF. A false positive would occur when the rhythm is anything but VT/VF (e.g., normal sinus rhythm (NSR), sinus tachycardia, atrial fibrillation, atrial flutter, electrical noise, e.g., due to mypotentials, electromagnetic interference (EMI), a loose set screw for a leadwire, a broken leadwire, etc.) and the detection algorithm erroneously declares it as VT/VF. A true negative would occur when the rhythm is anything but VT/VF (e.g., normal sinus rhythm (NSR), sinus tachycardia, atrial fibrillation, atrial flutter, electrical noise, e.g., due to mypotentials, electromagnetic interference (EMI), a loose set screw for a leadwire, a broken leadwire, etc.) and the detection algorithm correctly declares it as not VT/VF.

Ideally, a cardiac rhythm management device would have both 100% sensitivity and 100% specificity. However, it is well known in the art that for practical cardiac rhythm management devices, there exists a tradeoff between sensitivity and specificity, such that no practical detection scheme can obtain the ideal. As discussed above, existing implantable defibrillator/pacers are typically targeted toward patients with a history or high risk of life-threatening VT/VF episodes. Because of the severe (indeed life-threatening) consequences of failing to treat a VF episode, for example, existing defibrillator/pacers are typically configured to maximize sensitivity to VT/VF. To accomplish this, such devices typically sacrifice specificity. That is, they will generally tolerate the delivery of inappropriate counter-shocks (i.e., a lower specificity) if needed to maintain the desired high sensitivity. This ensures that virtually no VF episode will go untreated. It is true that many such defibrillator/pacers go through great lengths to improve the specificity to avoid inappropriately delivering a painful counter-shock to the patient. Still, such specificity enhancements typically are a secondary consideration—specificity cannot be increased if doing so would cause an appreciable number of VF episodes to go untreated—the potential consequences are too severe, particularly for a tachyarrhythmia patient population.

Bradycardia patients, on the other hand, typically receive a pacer without defibrillation capability, as presently called for by standard clinical, health insurance, and government reimbursement guidelines. However, a significant number of pacemaker patients die from VF and polymorphic VT—even if no such previous episodes have been diagnosed. Such patients are ineligible for a defibrillator/pacer device, however, they could benefit from defibrillation therapy. As discussed above, however, existing defibrillator/pacer devices, however, are typically designed as defibrillators with backup pacing capability—they are not intended for bradycardia patients and, moreover, because of the needs of the tachycardia patient population for which they are designed, they are not well suited for bradycardia patients.

In sum, the present inventors have recognized a need in the art for improved cardiac rhythm management devices having both pacing and defibrillation therapies.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
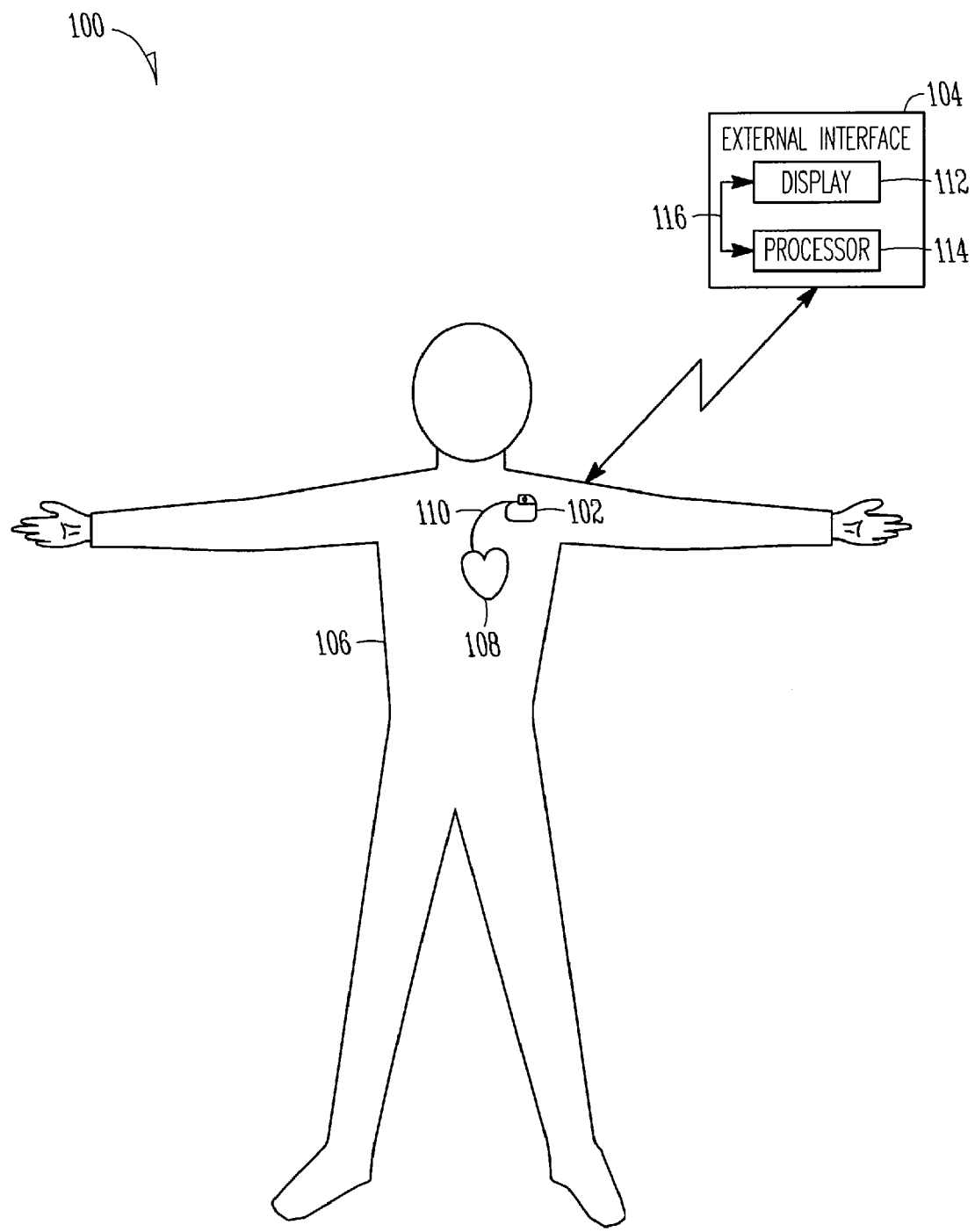
FIG. 1 is a schematic diagram illustrating generally one example of portions of a cardiac rhythm management system.

In the following detailed description, reference is made to the accompanying drawings which form a part hereof, and in which is shown by way of illustration specific embodiments in which the invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

Introduction

Today, a significant number of pacemaker patients (an estimated 12-30%) die from ventricular fibrillation (VF) and polymorphic ventricular tachyarrhythmias (PVTs). Sudden cardiac death (SCD) survival rates outside of the hospital are typically quite low. However, such patients are typically not indicated for combined defibrillator/pacers. Therefore, according to conventional clinical practice and reimbursement guidelines, they do not receive a device with defibrillation capability, even though such capability could prevent such deaths. Moreover, existing combined defibrillator/pacers are not designed for a bradyarrhythmia (pacemaker) population. They are instead designed for a tachyarrhythmia-prone patient population, and may therefore be unsuitable for a bradyarrhythmia patient population. For example, devices directed at the tachyarrhythmia-prone population typically have a propensity to deliver "false positive" antitachyarrhythmia therapy, such as defibrillation shocks. This has adverse physical and psychological consequences for bradyarrhythmia patients.

For the bradyarrhythmic/pacemaker patient population that is not otherwise indicated for an implantable cardioverter/defibrillator (ICD), patients with coronary artery disease are particularly at risk of SCD. Such patients with compromised ejection fractions (EFs) are also at increased risk of SCD. Another risk factor is a prior myocardial infarct (MI) with an EF>30% (such a patient having an EF<30% would typically already be indicated for a combination defibrillator/pacer). Another type of at-risk patient would have an EF=30% and would be non-ischemic. Another type of at-risk patient would have a documented history of nonsustained ventricular tachyarrhythmia (VT). Another risk factor would be a patient that meets the New York Heart Association (NYHA) Class II+classification criteria. Another type of at-risk patient would have multiple cardiac risk factors (defined as two or more of the following: obesity, smoker, diabetes, hypertension, high cholesterol, or a family history of SCD). In sum, there exist bradyarrhythmic patients who are not otherwise indicated for an ICD, but who may still obtain some benefit from antitachyarrhythmia therapy, such as antitachyarrhythmia pacing (ATP) or a defibrillation shock.

EXAMPLES

FIG. 1 is a schematic diagram illustrating generally one example of portions of a cardiac rhythm management system 100. In this example, the system 100 includes an implantable or other cardiac rhythm management (CRM) device 102. The system 100 also typically includes a programmer or other external interface device 104 permitting wireless or other communication with the CRM device 102. In the example of FIG. 1, the CRM device 102 is implanted in a pectoral region of a patient 106. The CRM device 102 in this example includes an electronics unit that is coupled to the patient's heart 108, such as by one or more intravascular or other leads 110. Each such lead 110 typically includes one or more electrodes for contacting a desired location within the patient 106, such as for sensing one or more intrinsic electrical heart signals, for delivering one or more contraction-evoking (e.g., pacing or cardiac resynchronization) stimulations, for delivering one or more shocks for terminating a tachyarrhythmia episode, or for sensing impedance to detect respiration, or the like.

Figure 2:
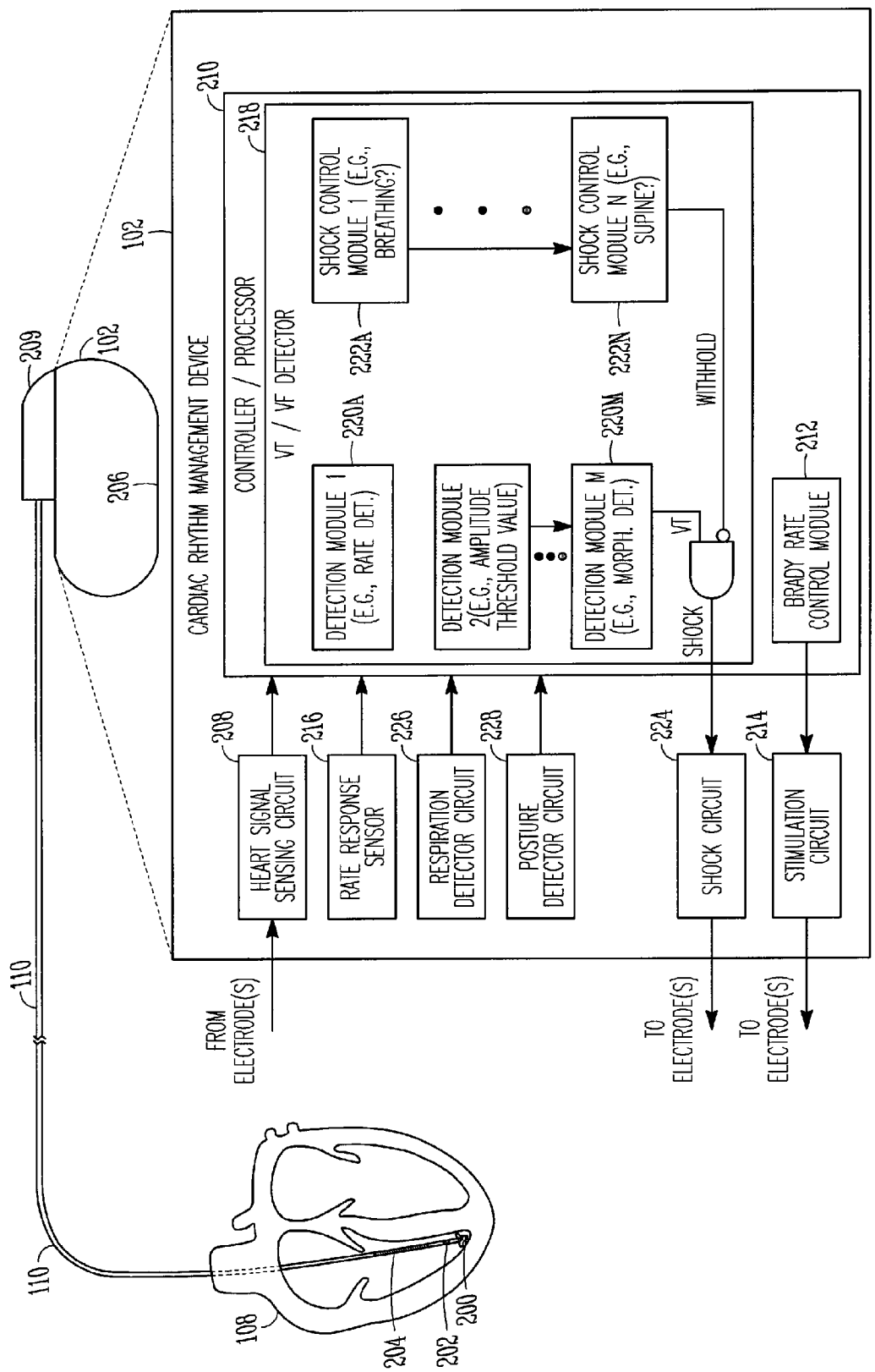
FIG. 2 is a schematic diagram illustrating further details of one example of portions of the system.

FIG. 2 is a schematic diagram illustrating further details of one example of portions of the system 100. In this example, a distal portion of the lead 110 is located in a right ventricle of the heart 108 and includes one or more electrodes such as a distal tip electrode 200, a slightly more proximal ring electrode 202, and an even slightly more proximal coil or other shock electrode 204. However, the system 100 may additionally or alternatively include other leads or electrodes that may be located elsewhere in or near the heart 108. The CRM device 102 typically includes electronics carried in a hermetically-sealed "can" 206. The can 206 typically includes one or more feedthroughs to a header 209. The header 209 typically includes one or more receptacles for receiving a proximal portion of one or more of the leads 110. One or both of the can 206 or header 209 may also include additional electrodes, such as for sensing intrinsic heart or other signals or for delivering stimulation or other energy to the patient 106.

The electronics unit of CRM device 102 typically includes a heart signal sensing circuit 208 to sense intrinsic electrical heart signals, such as depolarizations indicative of heart contractions. Such heart signals also include information about cardiac arrhythmias, such as VT/VF. The heart signal sensing circuit 208 typically includes one or more sense amplifier circuits to detect the heart signals, one or more filters for emphasizing depolarizations or other desired information, or for attenuating undesired information. In one example, the heart signal sensing circuit 208 also includes one or more peak or level detectors for detecting occurrences of heart depolarizations and providing corresponding responsive depolarization interrupts to a microprocessor or other controller 210. The controller 210 includes dedicated hardware or executable instructions to provide its functionality, such as to time the intervals between like depolarizations to determine a heart rate. In one example, the controller 210 includes a bradyarrhythmia rate control module 212 to determine whether the heart 108 needs a pacing-level electrical stimulation to induce or spatially coordinate a resulting heart contraction. The bradyarrhythmia rate control module 212 delivers one or more control signals to a stimulation circuit 214. In response, the stimulation circuit 214 delivers electrical energy via the electrodes to the heart 108 to evoke or assist in evoking or coordinating a responsive heart contraction. The bradyarrhythmia rate control module 212 typically receives information from a rate response sensor (e.g., accelerometer, minute ventilation, etc.) to indicate the patient's metabolic need for a particular heart rate and corresponding cardiac output.

In the example of FIG. 1, the controller 210 also includes a VT/VF detector 218 to determine whether a VT/VF is present and, if so, whether a shock should be delivered to treat the VT/VF. The determination of whether VT/VF is present is typically performed by one or more VT/VF detection modules 220A-M. Each detection module 220 typically includes its own particular criterion, criteria, or technique(s) for determining whether VT/VF is present. In one example, the VT/VF detector 218 also includes one or more shock control modules 222A-N. Each shock control module 222 typically includes its own particular criterion, criteria, or technique(s) for inhibiting shock delivery even if the VT/VF detection modules 220 indicate that a VT/VF is present. If a VT/VF is present, and the shock control modules 222 do not indicate that a shock should be withheld, then the VT/VF detector 218 of the controller 210 issues one or more control signals to a shock circuit 224 instructing it to deliver a shock to the heart 108 via the appropriate electrodes.

In one example, CRM device 102 is configured for a bradyarrhythmia-indicated patient population that may benefit from implantable defibrillation capability, instead of for a tachyarrhythmia-prone patient population. In one such example, the parameters controlling VT/VF detection or shock delivery/inhibition are factory-programmed or otherwise adjusted so that the VT/VF-shocking specificity of CRM device 102 exceeds its VT/VF detection sensitivity, thereby avoiding false shocks, albeit possibly at the expense of failing to treat a tachyarrhythmia needing treatment. This is a completely different and opposite paradigm than combined pacer/defibrillators intended for a tachyarrhythmia-prone patient population, in which sensitivity typically exceeds specificity in order to avoid failing to shock a treatable tachyarrhythmia. In one example, the parameters controlling VT/VF detection or shock delivery/inhibition are factory-programmed for a target bradyarrhyhmia patient population or otherwise adjusted such that the VT/VF-shocking specificity exceeds 95%, such as by exceeding 99%, or even by exceeding 99.5%. This is difficult to obtain in a practical system because increasing VT/VF-shocking specificity to such extreme values (e.g., especially above 95%), typically involves sacrificing VT/VF-detection sensitivity to below a value that would be regarded as acceptable for a tachyarrhythmia-prone patient population. However, the present inventors have recognized that including antitachyarrhythmia therapy, such as defibrillation shock capability, in a CRM device 102 that is intended for a bradyarrhythmia patient population, rather than a tachyarrhythmia-prone patient population, can advantageously reduce or avoid false shocks that would be unacceptable to the bradyarrhythmia patient population. The present device 102 permits VT/VF sensitivity to be less than VT/VF specificity, such as when the specificity exceeds 95%, 99%, or 99.5%. In another example, the specificity exceeds 95%, 99%, or 99.5% without regard to the sensitivity value.

In one example, the desired specificity is obtained by including appropriate detection modules 220 or shock control modules 222 and by properly programming their operative parameters, such as by using the external interface 104 at the factory or in the field. In one example, the desired specificity is obtained by factory programming the default values of such parameters. However, the user is permitted to alter the specificity, such as by further programming the values of such parameters away from their default values.

In one example, a detection module 220 includes a rate detector module 220A. In one example, the rate detector module 220A deems a VT/VF arrhythmia to be present only if a detected heart rate exceeds a high rate threshold value, such as a high rate threshold value that is in a range between about 200 beats per minute and about 250 beats per minute. In one example, the high rate threshold value is equal to 220 beats per minute. Therefore, in this example, only heart rhythms with a heart rate that exceeds 220 beats per minute will be deemed a VT/VF arrhythmia by such a detection module 220A. The particular high rate threshold value of the rate detector of detection module 220A can be programmably adjusted to a higher or lower value to obtain (or to help obtain) the desired specificity.

In another example, the one or more detection modules 220 include a morphology detection module 220M. In one example, the morphology detection module 220M compares a morphology of the detected heart signal against a template morphology, such as to classify whether a detected heart rhythm is a VT/VF rhythm that should be shocked. In one example, one or more parameters of such a morphology detection module 220M is adjusted to obtain (or to help obtain) the desired specificity. An example of such a parameter would be a correlation coefficient threshold value, where a correlation coefficient between the detected heart rhythm and the template morphology is computed and compared to the threshold value. By decreasing the amount of required correlation between a detected tachyarrhythmia and a template indicative of a non-shockable tachyarrhythmia, a specificity of shock delivery is increased. Alternatively, by increasing the amount of required correlation between a detected tachyarrhythmia and a template indicative of a shockable tachyarrhythmia, a specificity of shock delivery is increased.

In another example, a sensing control detection module 220B is used to control how ventricular depolarizations are sensed by the heart signal sensing circuit 208, such as to increase the specificity of detecting a shockable ventricular tachyarrhythmia. In one example, the sensing control detection module 220B establishes a higher amplitude level-detection threshold on the intrinsic ventricular cardiac signal sensed by the heart signal sensing circuit 208 for declaring the detection of a ventricular depolarization. For example, a typical ventricular depolarization level-detection threshold is set at about 0.3 mV. When the intrinsic cardiac signal exceeds 0.3 mV, a detected ventricular depolarization is declared. However, for the present increased shockable VT/VF arrhythmia specificity, the ventricular depolarization level-detection threshold is instead set between about 0.6 mV and 2.5 mV, such as at about 1.1 mV, such that a detected ventricular depolarization is declared only when the intrinsic ventricular cardiac signal level exceeds the threshold value (e.g., 1.1 mV). This improves noise rejection of spurious myopotentials and other noise. This increases the specificity of detecting ventricular depolarizations, which, in turn, increases the specificity of detecting and declaring a shockable VT/VF arrhythmia. In one example, the actual ventricular depolarization amplitude level-detection threshold value is established by sensing the noise floor of the intrinsic ventricular cardiac signal, and then setting the amplitude level-detection threshold value above the sensed noise floor.

Another example improves specificity by increasing the time duration that a VT/VF signal must persist at the heart signal sensing circuit 208 in order for the VT/VF arrhythmia episode to be declared present. In one example, this time duration is increased from a typical value of about 1 second (for a defibrillator/pacer intended for the tachyarrhythmia population) to greater than a threshold value that exceeds 15 seconds (e.g., a threshold of 15 seconds, 20 seconds, 25 seconds, 30 seconds, etc.).

In general, there are many types of detection modules 220 that can be used to detect a ventricular arrhythmia such as VT/VF, and the various operative parameters of such modules can be programmed to obtain the desired specificity. Moreover, such detection modules 220 can be used conjunctively to further increase specificity, such as to obtain a specificity that exceeds the sensitivity, as discussed above. Thus, the rate and morphology detectors discussed above are merely representative illustrative examples of the types of detection modules 220 that can be used in the present system 100.

The example of FIG. 2 also includes shock control modules 222 to inhibit shock delivery under certain circumstances, even if a VT/VF is detected. This further enhances the specificity of shock delivery of the CRM device 102. In one example, a shock control module 222A determines whether a patient is breathing, and inhibits shock delivery unless it is determined that the patient is not breathing. This further enhances specificity. In one example, information about whether the patient is breathing is obtained from a respiration detector circuit 226. In certain examples, the respiration detector circuit 226 uses thoracic or intracardiac impedance or the like to obtain information about the patient's breathing; the patient's breathing typically modulates such impedances.

In another example, a shock control module 222N determines whether a patient is supine, and inhibits shock delivery unless it determines that the patient is supine. This further enhances shock delivery specificity. In one example, information about whether the patient is supine is obtained from an accelerometer-based or other posture detector circuit 228.

In yet another example, a shock control module 222 implements an evoked-response detector to determine, in response to a detected VT/VF, whether a delivered pacing pulse evokes a responsive heart contraction. The evoked-response detector shock control module 222 inhibits shock delivery when such an evoked responsive heart contraction is detected and permits shock delivery when no such evoked responsive heart contraction is detected. In one example, the evoked-response detector shock control module 222 performs this function by issuing a control signal that directs the stimulation circuit 214 to issue a pacing pulse. The evoked-response detector shock control module 222 uses the heart signal sensing circuit 208 to look for a heart contraction that occurs in response to the issued pacing pulse. The issued pacing pulse is typically a large energy (i.e., large amplitude or pulsewidth) pacing pulse, which is sometimes referred to as a "safety pace," and which would be expected to capture the heart and result in a responsive heart contraction. The evoked-response detector shock control module 222 further enhances shock delivery specificity.

In another example, a cardiac impedance detector shock control module 222 is coupled to a cardiac impedance sensor circuit in the CRM device 102 to detect cardiac motion or cardiac output. The cardiac impedance detector shock control module 222 inhibits shock delivery unless the cardiac motion or cardiac output falls below a corresponding threshold value, thereby indicating a need for delivering a defibrillation shock to resuscitate the patient. In one example, cardiac impedance is detected by delivering a test current between two intracardiac electrodes and sensing a responsive voltage across the same (or different) two intracardiac electrodes. The resulting voltage signal is proportional to a cardiac impedance, which is affected and modulated by cardiac wall motion. An absence of wall motion, or a wall motion indicative of VT/VF rather than a well-coordinated ventricular contraction, provides further evidence that a defibrillation shock should be delivered. Similarly, a low cardiac output also provides further evidence that a defibrillation shock should be delivered. One measure of cardiac output is by the cardiac stroke volume multiplied by the heart rate, where the stroke volume is indicated by the modulation amplitude of the cardiac impedance signal resulting from ventricular contractions. By qualifying defibrillation shock delivery with such measurements, defibrillation shock delivery specificity is further enhanced.

In another example, a patient activity detector shock control module 222 is coupled to an accelerometer sensor circuit in the CRM device 102 to detect patient activity, that is, whether the patient is actively moving. The patient activity/motion detector shock control module 222 inhibits shock delivery when the patient is moving. This further enhances defibrillation shock delivery specificity.

In yet another example, the shock control module 222 includes a last-shocked timer to measure an elapsed time since a most recent shock was delivered, and to withhold shock delivery unless the elapsed time exceeds an elapsed time threshold value. This further increases shock delivery specificity, such as by reducing the occurrence of repeated false shocks. As an illustrative example, suppose that the elapsed time threshold value is set equal to 24 hours. In this example, if a shock has been delivered during the immediately preceding 24 hours, subsequent shocks are inhibited during the 24 hours after the preceding shock, even if a VT is detected during such time period. A further example distinguishes whether such shocks are being delivered in response to the same tachyarrhythmia episode, allowing multiple shocks to be delivered in response to the same tachyarrhythmia episode, but after that episode has been converted into a non-tachyarrhythmia rhythm, then requiring a time period in excess of the elapsed time threshold value (e.g., 24 hours, etc.) to elapse before any subsequent shocks are delivered.

Another example includes a shock control module 222 that automatically disables shock delivery after a predetermined number (e.g., one, two, etc.) of shocks have been delivered, or when the predetermined number of shocks have been delivered to treat a particular tachyarrhythmia episode. This reduces the number of false shocks and, therefore, further increases the shock delivery specificity.

Another example includes a shock control module 222 that permits a patient to disable shock delivery, such as after a predetermined number (e.g., one, two, etc.) of shocks have been delivered, or when the predetermined number of shocks have been delivered to treat a particular VT/VF episode. This reduces the number of false shocks and, therefore, further increases the shock delivery specificity. In one example, the patient disables shock delivery by placing a magnet near the implanted CRM device 102 to close a reed switch, thereby disabling further shock delivery. In another example, the patient disables shock delivery by using a bedside monitor, a portable communication device such as a "Patient Partner" adjunct external device, a programmer, or other external interface 104, which may have more restricted functionality than another programmer or other external interface 104 designed for use by a physician or other caregiver. In one example, the CRM device 102 only allows the patient to disable further shocks if at least one shock has been delivered to the patient. In an alternate example, the CRM device 102 allows the patient to enable or disable shock delivery regardless of whether any previous shocks have been delivered. For example, the patient may elect to disable shock delivery before engaging in activity resulting in myopotential noise that may trigger false positive shock delivery (e.g., painting a house), or during which time receiving a shock might be dangerous (e.g., standing on a ladder). The patient could then later re-enable shock delivery. In a further example, the extent to which a patient can control certain parameters, such as the ability to disable shock therapy, is in turn controlled by one or more separate physician-controlled parameters that determine the level of patient access and control over this or other functions of the CRM device 102.

Another example includes a shock control module 222 that includes a duration timer to measure an elapsed time duration since an onset of the VT/VF episode, and to inhibit shock delivery until the elapsed time duration since the onset of the tachyarrhythmia episode exceeds a duration threshold value that is in a range of between about 10 seconds and about 60 seconds, such as a value of 20 seconds, a value of 30 seconds, etc. This further increases the shock delivery specificity of the CRM device 102, because a VT/VF episode that does not continue for a period of time that exceeds the duration threshold value will not be shocked. In one further example, the CRM device 102 includes a beeper, vibrator, or other device for generating a warning to the patient that a defibrillation shock is about to be delivered. The technique for warning that a shock is about to be delivered can also be the same as one or more of the above-described techniques that a shock has already been delivered, or can be different so that the patient can discern between the incipient-shock warning and the shock-delivered notification. In certain embodiments, this warning allows the patient to disable the incipient shock delivery, such as by tapping the body (e.g., in a predetermined pattern, such as 3 taps separated by one second each) near where the CRM device 102 is implanted in a manner that can be detected and recognized by an accelerometer included within the CRM device 102, such that the shock delivery can be disabled.

In another example, the VT/VF detector 218 uses separate first and second channels of the heart signal sensing circuit 208 for detecting a VT/VF, thereby further enhancing the shock delivery specificity of the CRM device 102 by reducing the likelihood that noise (e.g., myocardial signals, electromagnetic interference, etc.) is erroneously sensed as a VT/VF episode. In one such example, the first heart rate signal sensing channel is coupled to at least one different electrode (e.g., shock coil electrode 204) than the second heart rate sensing channel (e.g., coupled to tip electrode 200). For example, where the detection module 220 includes a high rate detection module 220A, as discussed above, in one example the detected heart rate must exceed the high rate threshold (e.g., 220 beats per minute) on each of the first and second heart rate sensing channels.

In one example, one or more parameters of the one or more detection modules 220 or of the one or more shock control modules 222 or other portion(s) of the CRM device 102 are programmed to obtain a desired composite specificity (for example, a specificity that exceeds the sensitivity, or a specificity that exceeds 95%, 99%, and even 99.5%). In a further example, such parameters are also then programmed to provide a high sensitivity—but not at the expense of reducing the specificity below the target value to which it was programmed. In one example, the desired specificity is obtained by factory-programming such parameters to obtain an expected specificity as determined by previous testing, such as on an appropriate target patient population. In another example, these parameters are user programmable to obtain the desired specificity. In one example, the external interface 104 includes a display 112 that lists or otherwise displays one or more combinations of such parameters, along with an indication of the expected or projected specificity or sensitivity for that combination, such as can be determined from or estimated from prior testing on the appropriate target patient population. In a further example, the external interface 104 also includes a processor 114 coupled to the display by a node/bus 116. Among other things, the processor 114 controls the content that appears on the display 112. In one example, the external interface 104 receives user input specifying a target specificity, and the processor 114 automatically adjusts values of one or more of the parameters to obtain the target specificity by using stored specificity information corresponding to various parameter values or combinations of parameter values.

Although FIG. 2 has been illustrated above as separating VT/VF detection modules from shock control modules that inhibit shock delivery even if a VT/VF is detected, this separation into distinct functions is merely provided to help the reader's conceptualization of the present systems, devices, and methods. It should be understood that detection and inhibition can be blended. Moreover, a particular specificity is obtainable not merely from detection modules or shock control modules, but also or alternatively by implementation or adjustment of other portions of the CRM device 102. In one such illustrative example, the depolarization amplitude threshold of heart signal sensing circuit 208 is increased to increase the antitachyarrhythmia therapy delivery specificity. In another example, the device includes or adjusts an electromagnetic interference (EMI) mitigation circuit to improve specificity by reducing false positive VT/VF detection resulting from EMI.

In a further example, the CRM device 102 is configured to notify the patient that a shock has been delivered—since it is possible that the patient may not be aware of that event. As an illustrative example, the patient may be sleeping when a shockable VT/VF is detected, the shock may be delivered during sleep or unconsciousness, and the patient may have no memory of the shock later. Such notification that a shock has been delivered is particularly important, for example, for a patient with no previous history of VT/VF symptoms. For such a patient, the delivery of the high specificity shock to terminate a VT/VF episode will typically indicate that the patients disease symptoms have just dramatically changed, such that immediate consultation with a physician may be appropriate. There are a number of ways that such a notification can be provided. In one example, the CRM device 102 includes a beeper or other speaker or a vibrator to produce a distinctive pattern that continuously or intermittently notifies the patient that a shock has been delivered, such that a physician should be consulted as soon as possible. In another example, the CRM device 102 includes a telemetry circuit that communicates with an external device, such as a bedside monitor device or a "Partner" external device that is adjunct to the implantable CRM device 102, a repeater connected to a communications network for communication to an Advanced Patient Management (APM) computer system for managing various CRM devices 102 in different patients. The external device can notify the patient directly (e.g., with a visual or audible indicator), or indirectly (such as by a prerecorded telephone message or a telephone call from a customer relations representative, an e-mail message, etc.). The external device can also notify the patient's doctor that a shock has been delivered. Other examples of notification could include delivering intermittent or other high rate pacing or a low-energy ("tickle") shock to the patient to warn the patient that a high energy defibrillation shock has been delivered, or by appropriately adjusting other perceptible therapy that is safe to deliver to the patient and different enough from the patient's ordinary therapy such that it can be recognized by the patient as a warning that the shock has been delivered.

Figures 3, 4:
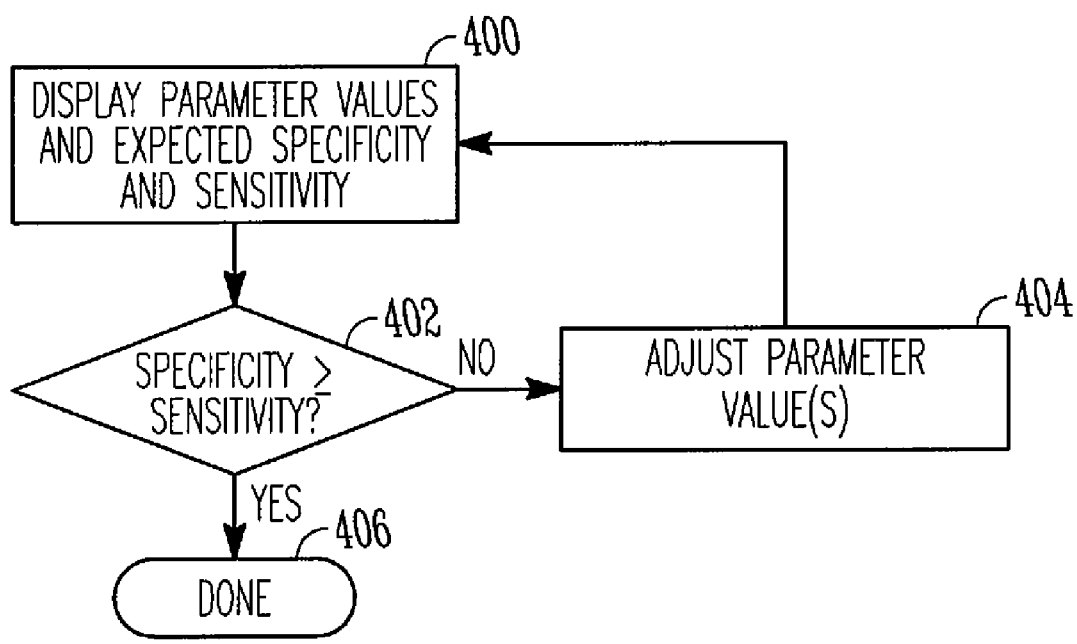
FIG. 3 illustrates one example of a method of adjusting specificity, either by a physician or other user, or at the factory manufacturing the CRM device.
FIG. 4 illustrates another example of a method of adjusting specificity.

FIG. 3 illustrates one example of a method of adjusting specificity, either by a physician or other user, or at the factory manufacturing the CRM device. At 300, parameter values associated with the one or more detection modules 220 or the one or more shock control modules 222 or other modules are displayed, such as on a computer monitor or other display 112, along with the expected specificity yielded by such combination of parameters. At 302, if the specificity is not greater than or equal to a target value, then one or more of the parameter values is reprogrammed or otherwise adjusted at 304, and process flow returns to 300 to display the new parameter values and expected specificity. At 302, if the specificity is greater than or equal to the target value, then the process is deemed complete at 306.

FIG. 4 illustrates another example of a method of adjusting specificity, either by a physician or other user, or at the factory manufacturing the CRM device. At 400, parameter values associated with one or more detection modules 220 or the one or more shock control modules 222 or other modules are displayed, such as on a computer monitor or other display 112, along with the expected specificity and sensitivity yielded by such combination of parameters. At 402, if the specificity does not exceed the sensitivity, then one or more of the parameter values is reprogrammed or otherwise adjusted at 404 and process flow returns to 400 to display the new parameter values and expected sensitivity and specificity. Otherwise, at 402, if the specificity exceeds the sensitivity, then the process is deemed complete at 406.

Figure 5:
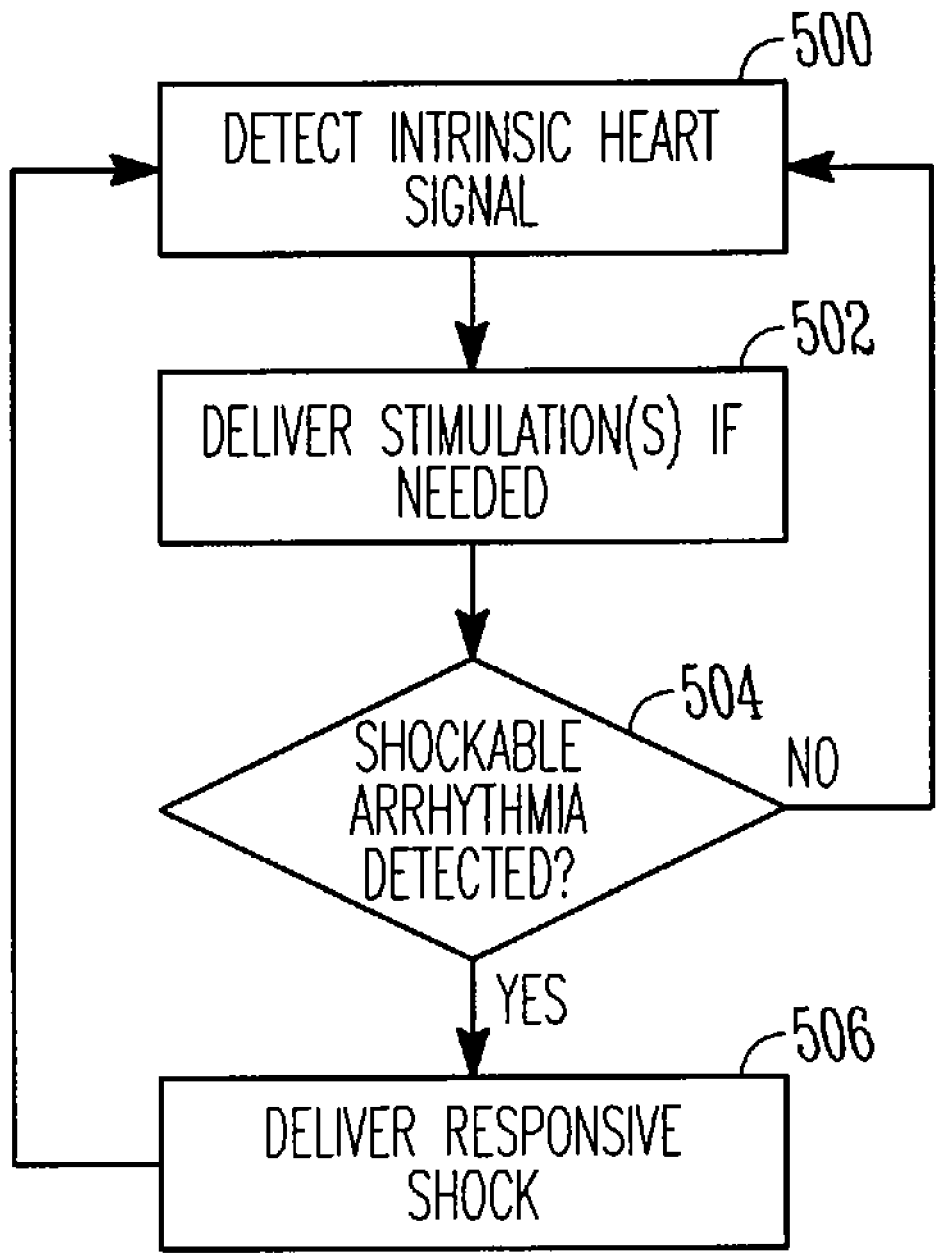
FIG. 5 illustrates one example of using a CRM device.

After the parameters are appropriately adjusted to obtain the desired specificity, as discussed above, the CRM device 102 is used. One example of using the CRM device 102 is illustrated in FIG. 5. At 500, at least one intrinsic electrical heart signal is detected from a heart of a patient. In one example, this is a ventricular signal that, at least during normal ventricular rhythms, includes QRS complexes indicative of ventricular depolarizations. Such ventricular signals also include discernable characteristics indicative of ventricular tachyarrhythmias, such as a ventricular fibrillation or polymorphic ventricular tachyarrhythmia (PVT) episode to be treated by an electrical shock to the heart. At 502, one or more stimulations are delivered to the heart, if needed to treat a bradyarrhythmia or as part of a cardiac resynchronization therapy (CRT) that is intended to improve spatial coordination of the heart contraction to improve cardiac output. Any such stimulations are delivered at an energy level (e.g., at a pacing-type energy level) that is appropriate to evoke or assist in evoking a responsive heart contraction. At 504, a determination is made of whether a shockable arrhythmia is detected. Examples of a shockable arrhythmia include ventricular fibrillation (VF) or a shockable polymorphic ventricular tachycardia. This detection is performed using a technique having a specificity and a sensitivity, such as from a particular combination of parameters used in detecting the shockable arrhythmia and in delivering/inhibiting shock therapy. In one example, the specificity exceeds the sensitivity. In one example, the determination of whether a shockable arrhythmia exists includes (or, alternatively, consists of) determining whether a ventricular heart rate exceeds a high rate threshold value, such as 220 beats per minute. At 504, if a shockable arrhythmia is detected then, at 506, a shock is delivered in response to the VT/VF, either alone or in combination with one or more other triggers. The shock is intended to terminate the VT/VF such that the heart reverts back to a non-tachyarrhythmic rhythm. Process flow then returns to 500. At 504, if a shockable arrhythmia is not detected, then process flow returns to 500.

Figure 6:
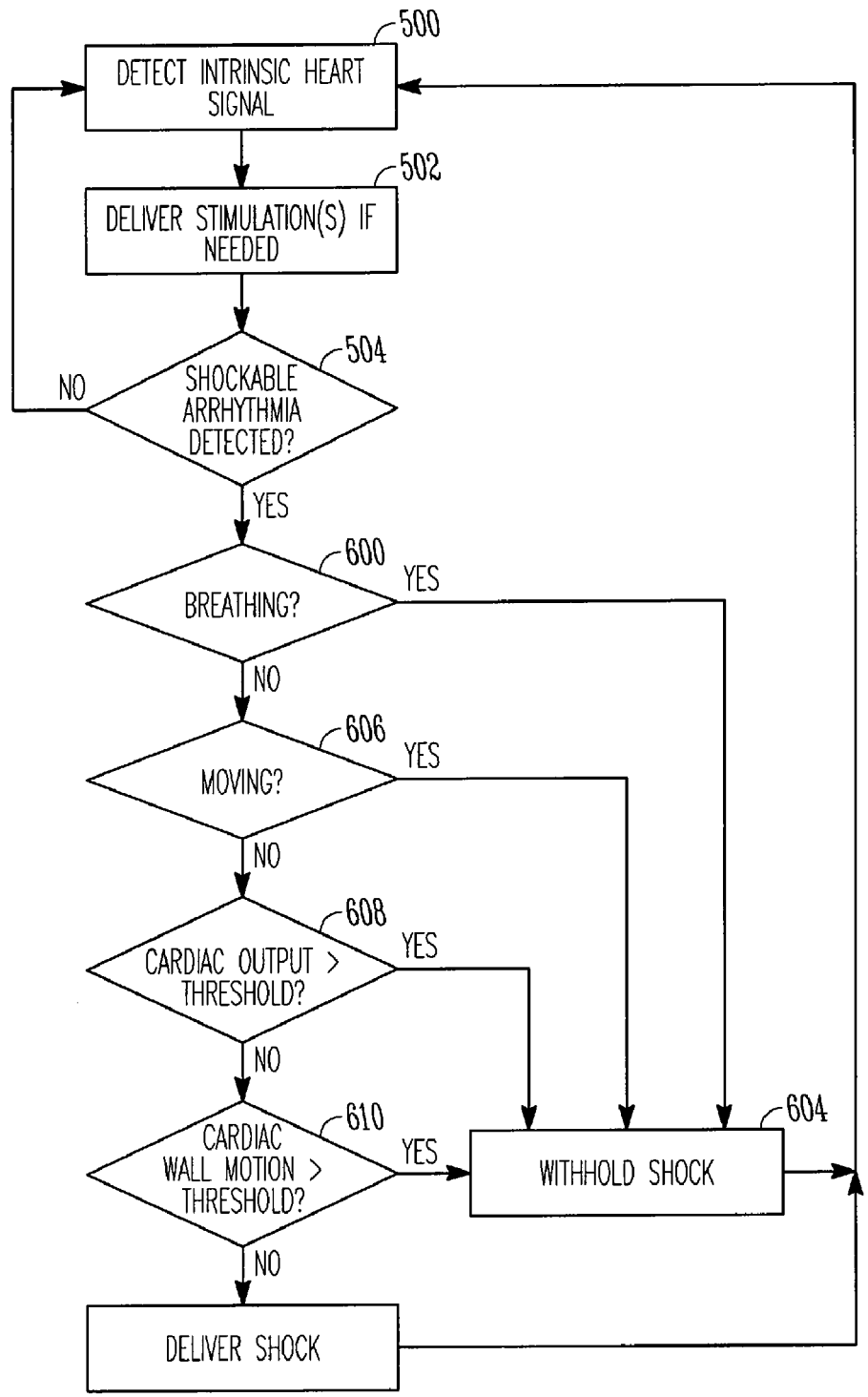
FIG. 6 illustrates one example of another technique of using the CRM device.

FIG. 6 illustrates one example of another technique of using the CRM device 102. This example includes acts at 500, 502, and 504 that are similar to those described above with respect to FIG. 5. If a shockable arrhythmia is detected at 504, then one or more determinations is made as to whether to inhibit the shock delivery. For example, at 600, it is determined whether the patient is breathing. If the patient is breathing, then a shock is withheld, at 604, and process flow returns to 500. At 600, if the patient is not breathing, then zero or more further determinations are made as to whether to inhibit the shock delivery. For example, at 606, it is determined whether the patient is moving (for example, by comparing an accelerometer output level to a threshold value). If the patient is moving, then a shock is withheld, at 604, and process flow returns to 500. At 606, if the patient is not moving, then zero or more further determinations are made as to whether to inhibit the shock delivery. For example, at 608, it is determined whether the patient's cardiac output exceeds a threshold value (for example, by using a cardiac impedance sensor). At 608, if the patient's cardiac output exceeds the threshold value, then a shock is withheld at 604, and process flow returns to 500. At 608, if the patient's cardiac output does not exceed the threshold value, then zero or more further determinations are made as to whether to inhibit the shock delivery. For example, at 610, it is determined whether cardiac wall motion exceeds a threshold value. At 610, if the cardiac wall motion exceeds the threshold value, then a shock is withheld at 604, and process flow returns to 500. At 610, if the cardiac wall motion does not exceed the threshold value, then zero or more further determinations are made as to whether to inhibit the shock delivery. In the example of FIG. 6, after all shock inhibition decisions indicate that shock delivery is not to be inhibited at 604, then at 612, a defibrillation shock is delivered. Process flow then returns to 500.

Figure 7:
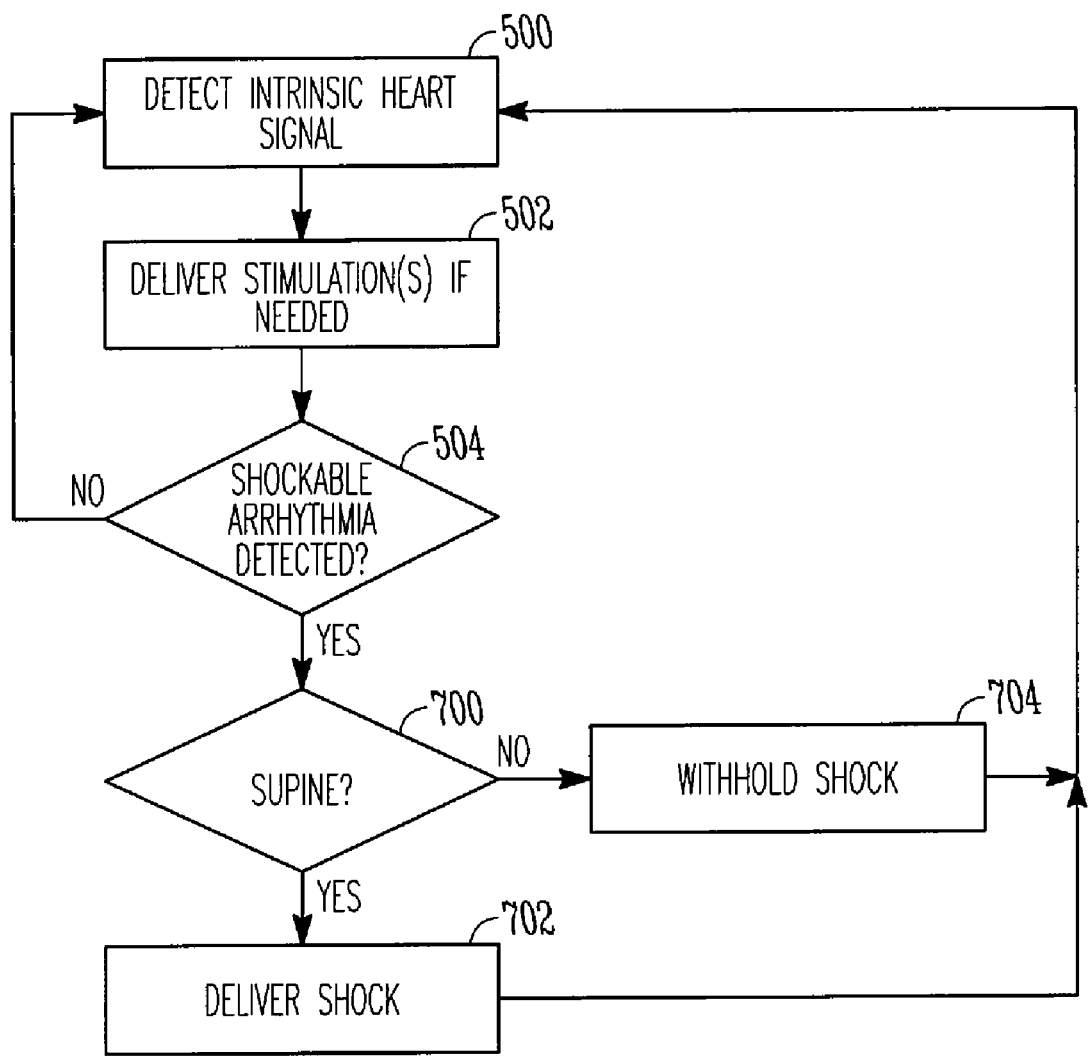
FIG. 7 illustrates one example of another technique of using the CRM device.

FIG. 7 illustrates one example of another technique of using the CRM device 102. This example includes acts at 500, 502, and 504 that are similar to those described above with respect to FIG. 5. If a shockable arrhythmia is detected at 504, then at 700, it is determined whether the patient is supine. If the patient is supine, then a shock is delivered at 702, and process flow then returns to 500. Otherwise the shock is withheld at 704 and process flow returns to 500. In the example of FIG. 7, one or more other shock inhibition determinations can be applied conjunctively with the determination of whether the patient is supine, such as described above with respect to FIG. 6, for example. This further enhances the specificity of the shock delivery.

Figure 8:
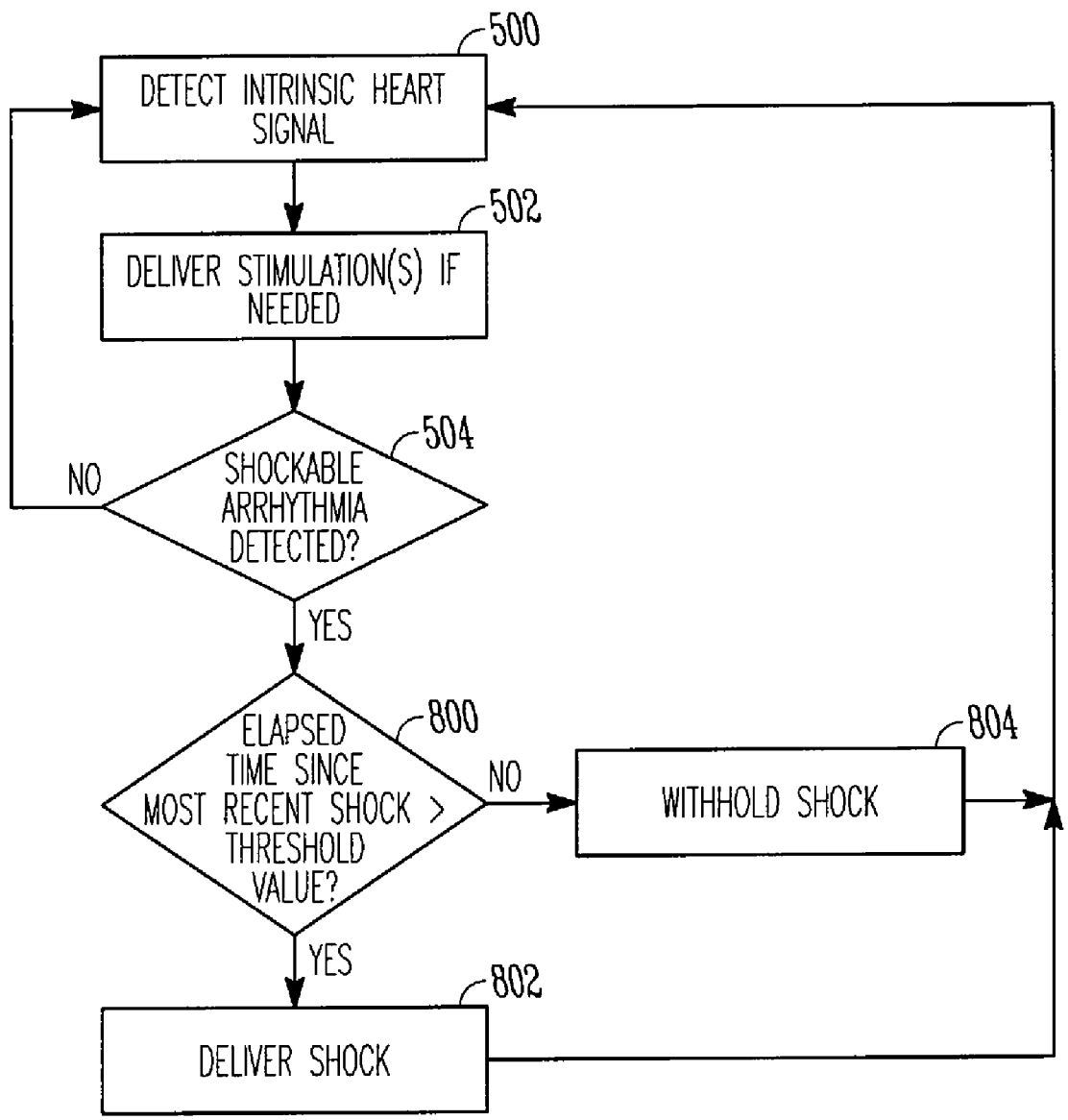
FIG. 8 illustrates one example of another technique of using the CRM device.

FIG. 8 illustrates one example of another technique of using the CRM device 102. This example includes acts at 500, 502, and 504 that are similar to those described above with respect to FIG. 5. If a shockable arrhythmia is detected at 504, then at 800, it is determined whether an elapsed time since a most recent shock exceeds a threshold value (e.g., 24 hours). If so, a shock is delivered at 802, provided that it is not inhibited by another conjunctive shock control module 222, and process flow then returns to 500. Otherwise, the shock is withheld at 804, and process flow returns to 500. In the example of FIG. 8, one or more other shock inhibition determinations can be applied conjunctively with the determination at 804, such as described above with respect to FIG. 6, for example. This further enhances the specificity of the shock delivery.

Figure 9:
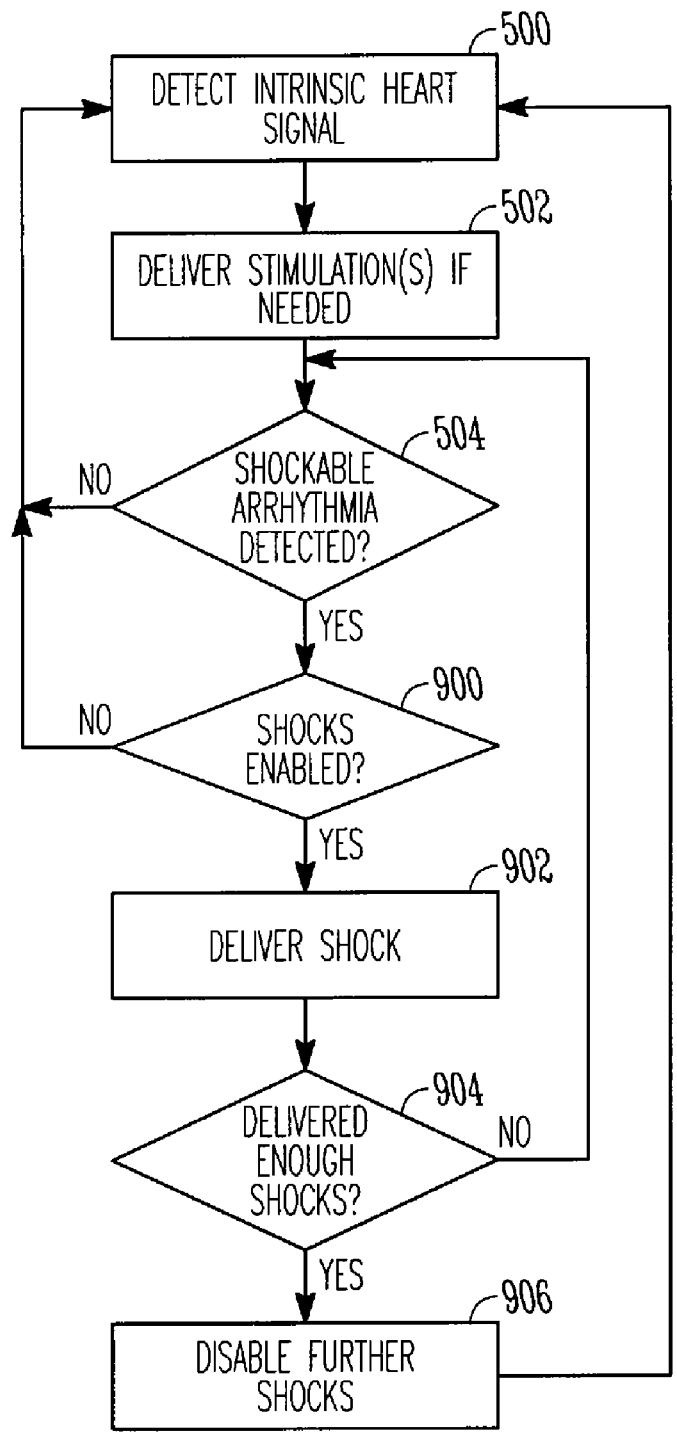
FIG. 9 illustrates one example of another technique of using the CRM device in which further shocks are disabled after delivering a defibrillation shock.

FIG. 9 illustrates one example of another technique of using the CRM device 102. This example includes acts at 500, 502, and 504 that are similar to those described above with respect to FIG. 5. If a shockable arrhythmia is detected at 504, then at 900 it is determined whether shocks are enabled. At 900, if shocks are enabled, then a shock is delivered at 902, otherwise process flow returns to 500. After a shock is delivered at 902, it is determined at 904 whether enough shocks have been delivered to treat that arrhythmia episode. At 904, if enough shocks have been delivered to treat that tachyarrhythmia episode, then further shocks are automatically disabled at 906. Further shock delivery is then inhibited until shocking is re-enabled by a physician. At 904, if enough shocks have not been delivered to treat that tachyarrhythmia episode (such as when a predetermined number of shocks has not been reached), then process flow returns to 504.

In an alternative example, instead of the device 102 automatically disabling shock delivery at 906, the patient is permitted to disable shock delivery at 906. In one example, the patient is only permitted to disable shock delivery if at least one shock has been delivered to treat at least one tachyarrhythmia episode. In a further example, the patient is also permitted to re-enable shock delivery, if desired.

Figure 10:
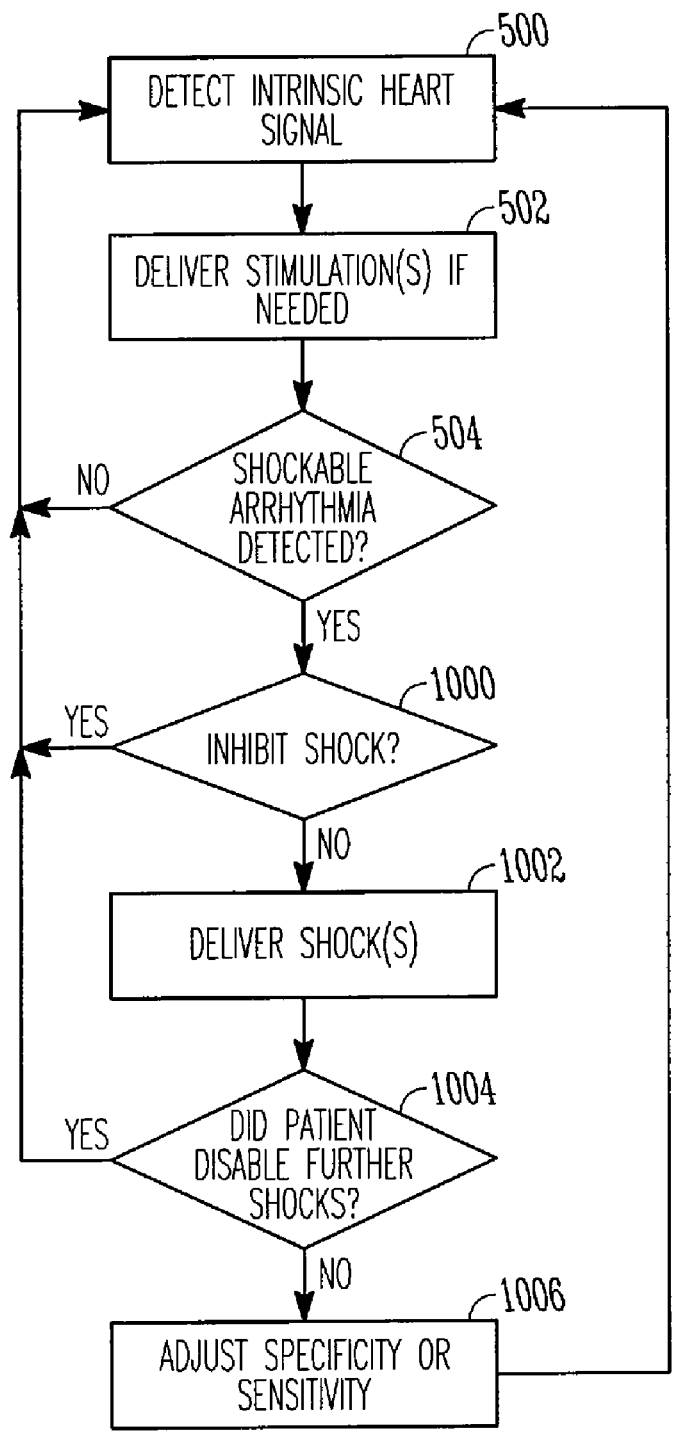
FIG. 10 illustrates one example of another technique of using the CRM device in which a specificity or sensitivity is automatically adjusted after delivering a defibrillation shock.

FIG. 10 illustrates one example of another technique of using the CRM device 102. This example includes acts at 500, 502, and 504 that are similar to those described above with respect to FIG. 5. If a shockable arrhythmia is detected at 504, then at 1000, the CRM device 102 determines whether the shock should be inhibited, such as by using one of the specificity enhancements described above. If this determination indicates that the shock should be inhibited for that particular detected arrhythmia, then a first shock inhibit flag is set. If this determination indicates that the shock should be inhibited for that particular detected arrhythmia as well as other subsequently detected arrhythmias (such as where shock delivery has been disabled by the patient or automatically by the CRM device 102, for example), then a second shock inhibit flag is set. If either shock inhibit flag is set, then process flow returns to 500. Otherwise, at 1002, one or more shocks is delivered to treat that tachyarrhythmia episode. After a predetermined number (e.g., 1, 2, etc.) of shocks is delivered at 1002, then, in one example, a patient is permitted to disable further shocks (or alternatively, the CRM device 102 automatically disables further shocks) by setting the second shock inhibit flag. At 1004, if the patient has disabled further shocks, then process flow returns to 500 with the second shock inhibit flag set to inhibit further shocks at 1000. Otherwise, at 1006, in one example, the CRM device 1002 automatically adjusts the specificity and sensitivity appropriate for a patient with a documented history of tachyarrhythmia (e.g., adjusting sensitivity>specificity), since the patient has now received at least one defibrillation shock in response to a detected tachyarrhythmia episode. In one example, the CRM device 102 also notifies the patient or doctor about the delivery of the defibrillation shock and the resulting change in status and in specificity or sensitivity. Then, process flow returns to 500.

The above description has particularly emphasized defibrillation shock as an antitachyarrhythmia therapy, at least part because the importance of specificity is perhaps easiest to understand in that context. However, the present document also envisions antitachyarrhythmia pacing (ATP) therapy or other antitachyarrhythmia therapy being delivered instead of or in addition to defibrillation shock therapy. For example, incorporating defibrillation shock therapy into a bradyarrhythmia therapy device opens up new possibilities for using ATP pacing for such a patient population, because such ATP pacing is fairly effective at terminating tachyarrhythmias, but presents a finite risk of inducing VF. Where the bradyarrhythmia therapy device includes defibrillation shock therapy, the risk of using ATP pacing to terminate a tachyarrhythmia is offset by the availability of a defibrillation shock.

Although the above techniques have been particularly described with respect to implementing antitachyarrhythmia therapy in a device that is tailored for the bradyarrhythmia population, certain of these specificity enhancements or other techniques will also be useful in an implantable cardioverter/defibrillator device that is intended for a tachyarrhythmia population, such as for improving shock delivery specificity. Likewise, certain of these specificity enhancements or other techniques will be useful in a "leadless" or other subcutaneously implantable cardioverter/defibrillator device, which may not include any pacing capability. Because such leadless ICDs typically do not include an electrode in close proximity to the heart, they typically must rely on "far-field" sensing, which increases the risk of false positive VT/VF detection, making the above-described specificity enhancements particularly valuable for such leadless ICDs.

Moreover, although the above description has emphasized techniques for tailoring a pacer/defibrillator for a bradyarrhythmia population, they are not limited to specially designing a pacer/defibrillator device for a bradyarrhythmia population. Instead, such techniques are also intended to be useful for retrofitting an existing defibrillator/pacer that was originally intended for a tachyarrhythmia population to tailor that existing defibrillator/pacer for use with a bradyarrhythmia patient or bradyarrhythmia patient population. In one such illustrative example, an existing multiple rate zone or other defibrillator/pacer is reprogrammed to use a single rate zone that declares a VT/VF if a detected heart rate exceeds a threshold value, such as a threshold value that is greater than or equal to 200 beats per minute (e.g., 210 bpm, 220 bpm, 230 bpm, 240 bpm, etc.). A defibrillation shock or other antitachyarrhythmia therapy is delivered if a detected VT/VF is declared.

Furthermore, although the above description has described antitachyarrhythmia therapy in terms of sensitivity and specificity, other alternative measures may also be useful. For example, the specificity described by Eq. 2 may present a practical difficulty because the occurrence of a true negative may be a difficult determination. Therefore, in one example, a "positive predictivity" metric is used as a surrogate for the above-described balance between specificity and sensitivity. The positive predictivity is described by Eq. 3:

Positive Predictivity=True Positives/(True Positives+ False Positives)   Eq. 3

The positive predictivity described by Eq. 3 has the practical advantage of being defined without regard to the occurrence of a true negative. A typical defibrillator/pacer that is designed for a tachyarrhythmia population, but that is used in a bradyarrhythmia patient population, will have a ratio of true positives to false positives of about 1:1. By contrast, in one example, the pacer/defibrillator of the present system is specifically tailored for the bradyarrhythmia population by configuring its ratio of true positives to false positives to equal or exceed about 3:1, such that the positive predictivity exceeds 75%. In some examples, the positive predictivity even exceeds 90%.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. An apparatus comprising:
   an implantable cardiac rhythm management device, the cardiac rhythm management device comprising:
      a heart signal sensing circuit to sense intrinsic electrical heart signals from a heart of a patient;
      a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity of ventricular tachyarrhythmia/fibrillation detection, and wherein the ventricular tachyarrhythmia/fibrillation detector circuit is configured such that the specificity exceeds the sensitivity without regard to an operator skill level, and in which the ventricular tachyarrhythmia/fibrillation detector circuit includes one or more shock control modules to determine whether a patient should be shocked, wherein the one or more shock control modules are individually or collectively programmable by one or more parameters, and wherein the one or more parameters are factory programmed to one or more corresponding default values such that the specificity exceeds the sensitivity in a target patient population;
      a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
      a stimulation circuit, coupled to the heart signal sensing circuit, the stimulation circuit configured to deliver to the heart a stimulation at an energy level appropriate to evoke or assist in evoking a responsive heart contraction.

2. The apparatus of claim 1, in which the specificity is greater than or equal to 99%.

3. The apparatus of claim 2, in which the sensitivity is less than 99%.

4. The apparatus of claim 2, in which the specificity is greater than or equal to 99.5%.

5. The apparatus of claim 4, in which the sensitivity is less than 99.5%.

6. The apparatus of claim 1, in which the one or more parameters is further programmable by a user.

7. The apparatus of claim 1, in which the cardiac rhythm management device further includes a telemetry circuit that is operatively communicatively coupled to a local or remote external programmer, and wherein the local or remote external programmer includes a user interface configured to permit programming of the one or more parameters of the one or more shock control modules.

8. The apparatus of claim 7, in which the user interface includes a display illustrating projected values of the specificity or the sensitivity corresponding to particular settings of one or more parameters of the implantable cardiac rhythm management device.

9. The apparatus of claim 1, in which the one or more shock control modules includes a respiration detector to determine whether the patient is breathing and to withhold shock delivery when the patient is breathing.

10. The apparatus of claim 1, in which the one or more shock control modules includes a posture detector to determine whether the patient is supine and to withhold shock delivery when the patient is not supine.

11. The apparatus of claim 1, in which the one or more shock control modules includes an evoked-response detector to determine, in response to a detected tachyarrhythmia or fibrillation, whether a delivered pacing pulse evokes a responsive heart contraction and to withhold shock delivery when an evoked responsive heart contraction is detected.

12. The apparatus of claim 1, in which the one or more shock control modules includes a high rate detection threshold to determine whether a detected heart rate exceeds a high rate detection threshold value that is in a range between about 200 beats per minute and 250 beats per minute and to withhold shock delivery unless the detected heart rate exceeds the high rate detection threshold value.

13. The apparatus of claim 1, in which the one or more shock control modules includes a last-shocked timer to measure an elapsed time since a most recent shock was delivered, and to withhold shock delivery unless the elapsed time exceeds an elapsed time threshold value.

14. The apparatus of claim 1, in which the one or more shock control modules is operable to automatically disable shock delivery after the cardiac rhythm management device has treated a tachyarrhythmia or fibrillation episode by delivering at least one shock.

15. The apparatus of claim 1, in which the one or more shock control modules is operable to permit the patient to enable or disable shock delivery.

16. The apparatus of claim 1, in which the one or more shock control modules is operable to permit the patient to disable shock delivery only after the cardiac rhythm management device has treated a tachyarrhythmia or fibrillation episode by delivering at least one shock.

17. The apparatus of claim 1, in which the one or more shock control modules includes a duration timer to measure an elapsed time duration since an onset of the tachyarrhythmia or fibrillation episode, and to withhold shock delivery until the time duration equals or exceeds a duration threshold value that is in a range between about 10 seconds and about 60 seconds.

18. The apparatus of claim 1, in which the one or more shock control modules is coupled to an impedance sensor to detect intracardiac impedance and to withhold shock delivery if the intracardiac impedance indicates that a heart wall motion level exceeds a heart wall motion threshold value or that a cardiac output is more than a cardiac output threshold value.

19. The apparatus of claim 1, in which the one or more shock control modules is coupled to an accelerometer to detect patient activity and to withhold shock delivery if the detected patient activity exceeds a patient activity threshold value.

20. The apparatus of claim 1, in which the heart signal sensing circuit includes first and second heart rate signal sensing channels, wherein the first heart rate signal sensing channel is operatively coupled to at least one different electrode than the second heart rate sensing channel, and wherein the one or more shock control modules includes a high rate detection threshold to determine whether a detected heart rate exceeds a high rate detection threshold value as determined from the first and second heart rate sensing channels.

21. The apparatus of claim 1, in which the heart signal sensing circuit includes a ventricular depolarization sensing threshold that is greater than or equal to a threshold value, wherein the threshold value is between about 0.6 millivolts and 2.5 millivolts.

22. The apparatus of claim 1, in which the implantable cardiac rhythm management device includes a flag to disable or enable shock delivery in response to a patient input.

23. The apparatus of claim 1, further comprising means for notifying the patient that a shock will be or has been delivered.

24. An apparatus comprising:
an implantable cardiac rhythm management device, the cardiac rhythm management device comprising:
  a heart signal sensing circuit to sense intrinsic electrical heart signals from a heart of a patient;
  a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, and in which the ventricular tachyarrhythmia/fibrillation detector circuit includes one or more shock control modules to determine whether a patient should be shocked, wherein the one or more shock control modules are individually or collectively programmable by one or more parameters, and wherein the one or more parameters are factory programmed to one or more corresponding default values such that the specificity exceeds the sensitivity in a target patient population, and in which the one or more parameters is further programmable by a user;
  a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
  a stimulation circuit, coupled to the heart signal sensing circuit, the stimulation circuit configured to deliver to the heart a stimulation at an energy level appropriate to evoke or assist in evoking a responsive heart contraction.

25. An apparatus comprising:
an implantable cardiac rhythm management device, the cardiac rhythm management device comprising:
  a heart signal sensing circuit to sense intrinsic electrical heart signals from a heart of a patient;
  a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules includes a respiration detector to determine whether the patient is breathing and to withhold shock delivery when the patient is breathing;
  a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
  a stimulation circuit, coupled to the heart signal sensing circuit, the stimulation circuit configured to deliver to the heart a stimulation at an energy level appropriate to evoke or assist in evoking a responsive heart contraction.

26. The apparatus of claim 25, wherein the one or more parameters are factory programmed to one or more corresponding default values such that the specificity exceeds the sensitivity in a target patient population.

27. An apparatus comprising:
an implantable cardiac rhythm management device, the cardiac rhythm management device comprising:
  a heart signal sensing circuit to sense intrinsic electrical heart signals from a heart of a patient;
  a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules includes a posture detector to determine whether the patient is supine and to withhold shock delivery when the patient is not supine;
  a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
a stimulation circuit, coupled to the heart signal sensing circuit, the stimulation circuit configured to deliver to the heart a stimulation at an energy level appropriate to evoke or assist in evoking a responsive heart contraction.

28. The apparatus of claim 27, wherein the one or more parameters are factory programmed to one or more corresponding default values such that the specificity exceeds the sensitivity in a target patient population.

29. An apparatus comprising:
an implantable cardiac rhythm management device, the cardiac rhythm management device comprising:
a heart signal sensing circuit to sense intrinsic electrical heart signals from a heart of a patient;
a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules includes an evoked-response detector to determine, in response to a detected tachyarrhythmia or fibrillation, whether a delivered pacing pulse evokes a responsive heart contraction and to withhold shock delivery when an evoked responsive heart contraction is detected;
a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
a stimulation circuit, coupled to the heart signal sensing circuit, the stimulation circuit configured to deliver to the heart a stimulation at an energy level appropriate to evoke or assist in evoking a responsive heart contraction.

30. The apparatus of claim 29, wherein the one or more parameters are factory programmed to one or more corresponding default values such that the specificity exceeds the sensitivity in a target patient population.

31. An apparatus comprising:
an implantable cardiac rhythm management device, the cardiac rhythm management device comprising:
a heart signal sensing circuit to sense intrinsic electrical heart signals from a heart of a patient;
a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules includes a last-shocked timer to measure an elapsed time since a most recent shock was delivered, and to withhold shock delivery unless the elapsed time exceeds an elapsed time threshold value;
a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
a stimulation circuit, coupled to the heart signal sensing circuit, the stimulation circuit configured to deliver to the heart a stimulation at an energy level appropriate to evoke or assist in evoking a responsive heart contraction.

32. The apparatus of claim 31, wherein the one or more parameters are factory programmed to one or more corresponding default values such that the specificity exceeds the sensitivity in a target patient population.

33. An apparatus comprising:
an implantable cardiac rhythm management device, the cardiac rhythm management device comprising:
a heart signal sensing circuit to sense intrinsic electrical heart signals from a heart of a patient;
a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules is operable to automatically disable shock delivery after the cardiac rhythm management device has treated a tachyarrhythmia or fibrillation episode by delivering at least one shock;
a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
a stimulation circuit, coupled to the heart signal sensing circuit, the stimulation circuit configured to deliver to the heart a stimulation at an energy level appropriate to evoke or assist in evoking a responsive heart contraction.

34. The apparatus of claim 33, wherein the one or more parameters are factory programmed to one or more corresponding default values such that the specificity exceeds the sensitivity in a target patient population.

35. An apparatus comprising:
an implantable cardiac rhythm management device, the cardiac rhythm management device comprising:
a heart signal sensing circuit to sense intrinsic electrical heart signals from a heart of a patient;
a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules is operable to permit the patient to enable or disable shock delivery;
a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
a stimulation circuit, coupled to the heart signal sensing circuit, the stimulation circuit configured to deliver to the heart a stimulation at an energy level appropriate to evoke or assist in evoking a responsive heart contraction.

36. The apparatus of claim 35, wherein the one or more parameters are factory programmed to one or more corresponding default values such that the specificity exceeds the sensitivity in a target patient population.

37. An apparatus comprising:
an implantable cardiac rhythm management device, the cardiac rhythm management device comprising:
a heart signal sensing circuit to sense intrinsic electrical heart signals from a heart of a patient;
a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules is operable to permit the patient to disable shock delivery only after the cardiac rhythm management device has treated a tachyarrhythmia or fibrillation episode by delivering at least one shock;
a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
a stimulation circuit, coupled to the heart signal sensing circuit, the stimulation circuit configured to deliver to the heart a stimulation at an energy level appropriate to evoke or assist in evoking a responsive heart contraction.

38. The apparatus of claim 37, wherein the one or more parameters are factory programmed to one or more corresponding default values such that the specificity exceeds the sensitivity in a target patient population.

39. An apparatus comprising:
an implantable cardiac rhythm management device, the cardiac rhythm management device comprising:
a heart signal sensing circuit to sense intrinsic electrical heart signals from a heart of a patient;
a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules includes a duration timer to measure an elapsed time duration since an onset of the tachyarrhythmia or fibrillation episode, and to withhold shock delivery until the time duration equals or exceeds a duration threshold value that is in a range between about 10 seconds and about 60 seconds;
a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
a stimulation circuit, coupled to the heart signal sensing circuit, the stimulation circuit configured to deliver to the heart a stimulation at an energy level appropriate to evoke or assist in evoking a responsive heart contraction.

40. The apparatus of claim 39, wherein the one or more parameters are factory programmed to one or more corresponding default values such that the specificity exceeds the sensitivity in a target patient population.

41. An apparatus comprising:
an implantable cardiac rhythm management device, the cardiac rhythm management device comprising:
a heart signal sensing circuit to sense intrinsic electrical heart signals from a heart of a patient;
a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules is coupled to an impedance sensor to detect intracardiac impedance and to withhold shock delivery if the intracardiac impedance indicates that a heart wall motion level exceeds a heart wall motion threshold value or that a cardiac output is more than a cardiac output threshold value;
a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
a stimulation circuit, coupled to the heart signal sensing circuit, the stimulation circuit configured to deliver to the heart a stimulation at an energy level appropriate to evoke or assist in evoking a responsive heart contraction.

42. The apparatus of claim 41, wherein the one or more parameters are factory programmed to one or more corresponding default values such that the specificity exceeds the sensitivity in a target patient population.

43. An apparatus comprising:
an implantable cardiac rhythm management device, the cardiac rhythm management device comprising:
- a heart signal sensing circuit to sense intrinsic electrical heart signals from a heart of a patient;
- a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, in which the ventricular tachyarrhythmia/fibrillation detector circuit includes one or more shock control modules to determine whether a patient should be shocked, wherein the one or more shock control modules are individually or collectively programmable by one or more parameters, in which the one or more shock control modules is coupled to an accelerometer to detect patient activity and to withhold shock delivery if the detected patient activity exceeds a patient activity threshold value;
- a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation; and
- a stimulation circuit, coupled to the heart signal sensing circuit, the stimulation circuit configured to deliver to the heart a stimulation at an energy level appropriate to evoke or assist in evoking a responsive heart contraction.

44. The apparatus of claim 43, wherein the one or more parameters are factory programmed to one or more corresponding default values such that the specificity exceeds the sensitivity in a target patient population.

* * * * *